United States Patent [19]
Iwamoto

[11] Patent Number: 4,941,791
[45] Date of Patent: Jul. 17, 1990

[54] HANDY BOOKBINDER

[76] Inventor: Yasuhiko Iwamoto, 47-321, Chaya, Kyowa-cho, Ohbu-shi, Aichi-ken, Japan

[21] Appl. No.: 179,676
[22] Filed: Apr. 11, 1988

[30] Foreign Application Priority Data

| | | | |
|---|---|---|---|
| Apr. 15, 1987 | [JP] | Japan | 62-057027 |
| Apr. 21, 1987 | [JP] | Japan | 62-060540 |
| Sep. 9, 1987 | [JP] | Japan | 62-225855 |

[51] Int. Cl.[5] B42C 11/02; B42D 3/00; B42D 1/00; A61F 13/02
[52] U.S. Cl. 412/19; 281/29; 281/21.1; 428/40
[58] Field of Search 281/19 R, 21 R, 15 R, 281/29, 34; 412/4, 19; 428/40, 327; 402/3; 156/216

[56] References Cited

U.S. PATENT DOCUMENTS

| | | | |
|---|---|---|---|
| 3,133,750 | 5/1964 | Gerald | 281/29 |
| 3,215,450 | 11/1965 | Peterson et al. | 281/29 |
| 3,241,863 | 3/1966 | Paddack | 281/29 |
| 3,620,891 | 11/1971 | Jones, Sr. et al. | 281/21 R |
| 3,833,244 | 9/1974 | Heimann | 281/29 |
| 4,441,950 | 4/1984 | Lolli | 281/29 |
| 4,500,021 | 2/1985 | Bildusas | 428/40 |
| 4,636,432 | 1/1987 | Shibano et al. | 428/327 |
| 4,744,592 | 5/1988 | Barnette et al. | 281/34 |

*Primary Examiner*—Douglas D. Watts
*Assistant Examiner*—Paul M. Heyrana, Sr.
*Attorney, Agent, or Firm*—Lahive & Cockfield

[57] ABSTRACT

A handy bookbinder comprises at least one cover and a spine member. The spine member is formed with an adhesive face at one surface thereof. The spine member may or may not be attached to the cover at one side portion of its adhesive face. In the case where the spine member is attached to the cover, for use, sheets of paper to be held together are placed on the cover, and the spine member is bent and attached to one side of the whole of the sheets, and is attached to the uppermost sheet. Thus, the sheets are held together very easily as if a book were bound. If it is desired to add a new sheet or sheets to the book or to remove one or more of the existing sheets, the spine member may be stripped from the cover or the last sheet and the foregoing one side of the whole of the sheets. After the desired addition or removal, the book can be rebound in the same manner as described above.

7 Claims, 7 Drawing Sheets

F/G. 10
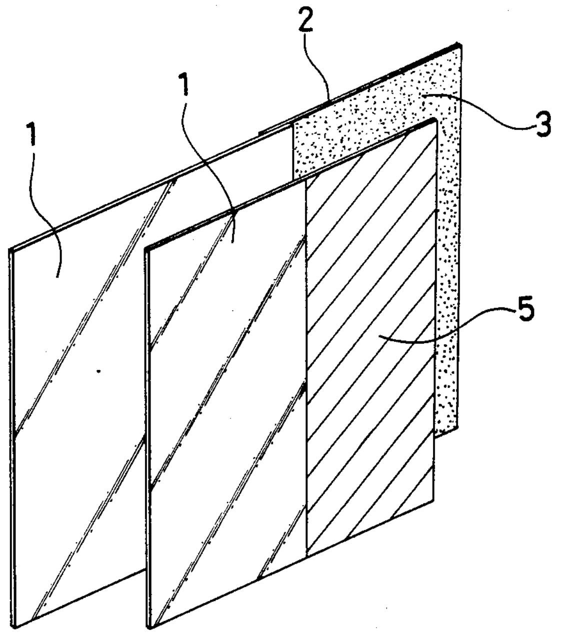
F/G. 11
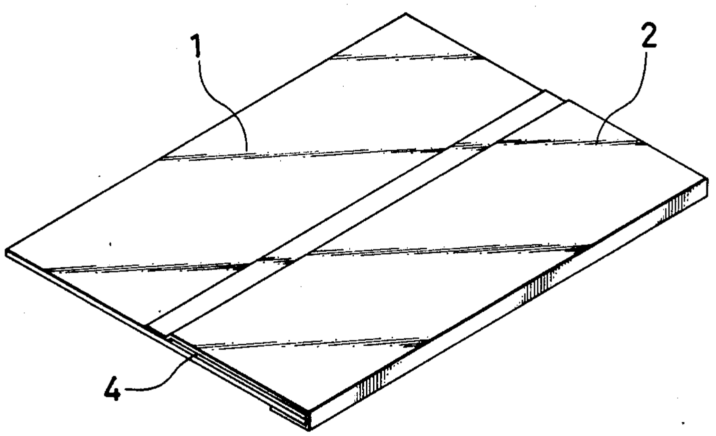

F/G. 17
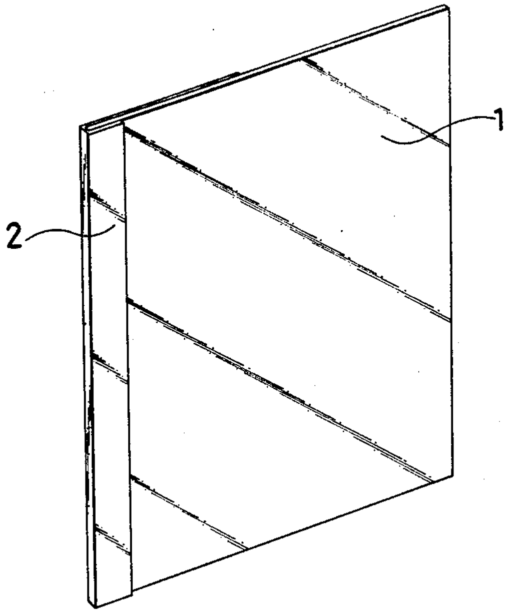

HANDY BOOKBINDER

FIELD OF THE INVENTION

This invention relates to handy bookbinders and, more particularly, to handy devices for holding together sheets of paper, such as various cards including postal cards, calling cards and business cards, photographs or the like.

BACKGROUND OF THE INVENTION

For example, with regard to business cards given by others, a file of plastic film with pockets in which to keep cards is commercially available. Such a file, however, has a much greater size than each card and, in addition, is relatively high in price. Also, it is not possible to view the reverse sides of the cards kept in such a file.

On the other hand, it is possible to keep the cards compactly by holding them together as if to bind a book. Also, if the cards are held together in such a manner, their reverse sides may be viewed. However, the work of holding together cards or similar materials has so far required an expensive instrument and expertise. So far, no device for holding such materials as if to bind a book has been available for personal use.

SUMMARY OF THE INVENTION

An object of the invention is to provide an inexpensive device for holding together sheets of paper, such as cards, photographs or the like, with substantially the same size as if to bind a book whereby such materials may be held together very easily and instantly with no expertise.

Another object of the invention is to provide a handy device for holding sheets of paper together with substantially the same size as if to bind a book whereby, after the sheets have been held together, one or more of the sheets may be removed or one or more new sheets may be added to the old sheets and the book may be rebound.

Still another object of the invention is to provide a handy device for holding together sheets of paper, such as cards, photographs or the like, with substantially the same size as if to bind a book, which device itself may be used as a postal card, a business card or the like.

BRIEF DESCRIPTION OF THE DRAWING

FIG. 10 is an exploded view of the bookbinder of FIG. 5. That is, in FIG. 10, the foregoing one side portion of the spine member of the bookbinder of FIG. 5 is detached from the foregoing one of the covers thereof;

FIG. 11 is a perspective view of a bookbinder according to a third preferred embodiment of the invention;

FIG. 17 shows that the bookbinder of FIGS. 11, 14 or 16, itself, may be employed as a postcard.

DETAILED DESCRIPTION OF THE PREFERRED EMBODIMENTS

Figure 1:
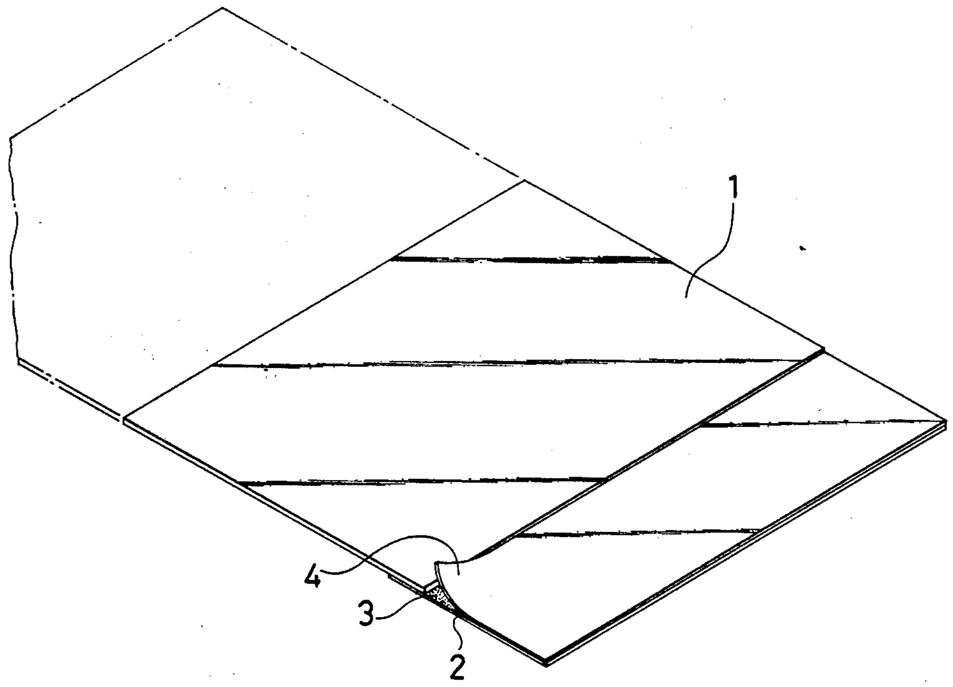
FIG. 1 is a perspective view of a bookbinder according to a first preferred embodiment of the invention.
Figure 3:
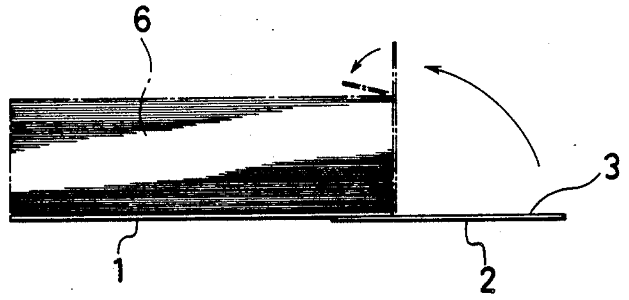
FIG. 3 shows how to hold sheets of paper, such as postal cards, together by using the bookbinder of FIGS. 1 or 2.
Figure 4:
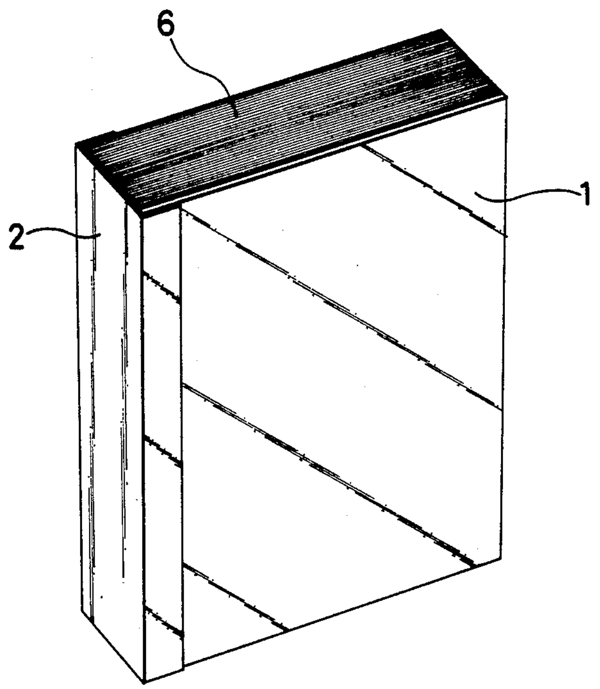
FIG. 4 shows sheets of paper, such as postal cards, held together with the bookbinder of FIGS. 1 or 2.

Referring now to FIG. 1 of the drawing, a bookbinder according to a first preferred embodiment of the invention comprises a cover 1 and a spine member 2. The cover 1 is of substantially the same size as sheets of paper to be held together. The spine member 2 is formed with an adhesive face 3 at one of its opposed surfaces. The spine member 2 is attached, at one side portion of its adhesive face 3, to one side portion of one of opposed surfaces of the cover 1. The portion of the spine member 2 not attached to the cover 1 has a width of 15 to 40 millimeters. A sheet of paper 4 is attached to the exposed portion of the adhesive face 3 of the spine member 2 to protect the exposed portion thereof against damage. For use, sheets of paper 6 to be held together, such as postal cards, are first placed on the cover 1 (FIG. 3), and then the protective paper 4 is peeled from the spine member 2. Then, as shown in FIG. 3, the spine member 2 is bent in a direction indicated by an arrow and is attached, at its adhesive face 3, to one side of the whole of the sheets 6. The side portion of the spine member 2 opposite to its side portion attached to the cover 1 is attached to the uppermost sheet. Thus the sheets 6 are held together as if a book were bound, as shown in FIG. 4. If, thereafter, it is desired to add a new sheet or sheets to the book or to remove one or more of the existing sheets 6 therefrom, preparations for the desired addition or removal can be made only by stripping one of the opposed side portions of the spine member 2 and the spine proper from the body of the book. And, after the addition or removal, the operation of FIG. 3 may be repeated to rebind the book.

Figure 2:
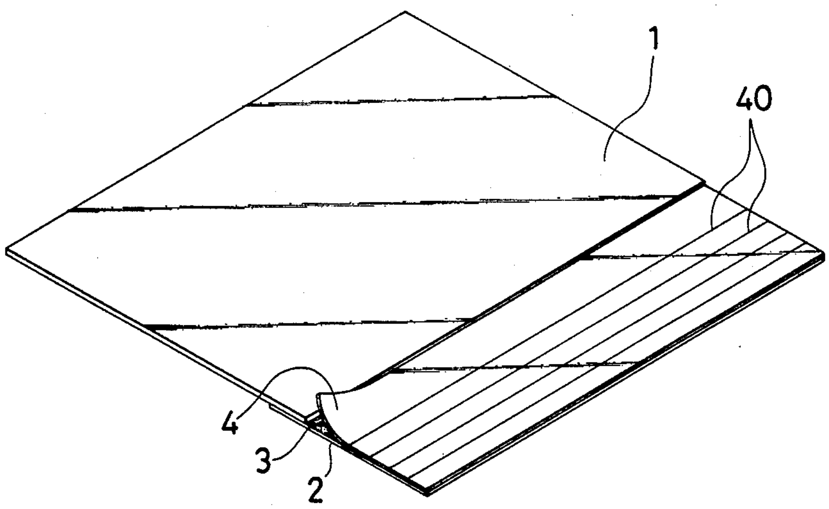
FIG. 2 shows a modification of the bookbinder of FIG. 1.

As shown in FIG. 2, a plurality of rows of short cuts may be made in the protective paper 4, in parallel with one side of the cover 1, to facilitate the detachment of the entire paper 4 from the spine member 2.

Also, if desired, an additional cover (not shown) may be provided which is to be placed on the uppermost sheet. In such a case, the side portion of the spine member 2 opposite to its side portion attached to the cover 1 is attached to the additional cover. Such an additional cover may be provided separately from the unit of FIGS. 1 or 2 or may be formed integrally therewith. In the latter case, as shown by a broken line of FIG. 1, such an additional cover may be formed continuously with the side of the cover 1 opposite to its side to which is attached the spine member 2. In such a case, a row of short cuts or similar means may be made where the two covers are to be separated.

The cover 1 is preferably made of a sheet of paper, a plastic sheet or the like with a relatively small thickness. As mentioned before, the cover 1 has substantially the same size as the sheets of paper to be held together. Therefore, when the sheets held together by the bookbinder are placed on a flat surface in their upright positions as shown in FIG. 4, they may rest directly on that surface at their bottoms and, hence, the possibility of their being detached from the spine may be minimized.

In the manufacture of the bookbinder of FIGS. 1 or 2, it is preferable to use a relatively long strip from which to cut out a number of covers 1 at their tops and bottoms. In such a case, a row of short cuts or similar means is preferably made in each portion in which to cut the strip.

As seen from the foregoing description, the bookbinder of FIGS. 1 or 2 has a very simple construction and, thus, is very inexpensive to manufacture. Also, by using the bookbinder, enables sheets of paper can be held together very easily and instantly. Any desired number of sheets not exceeding its maximum depending upon the width of the spine proper can be held together.

As mentioned before, after holding the sheets 6 together, the addition of a new sheet or sheets or the removal of one or more of the existing sheets 6 can be very easily made only by stripping one of the opposed side portions of the spine member 2 and the spine proper from the book. However, when stripping them, either the side portion of the spine member 2 or the cover 1 (or the last "page" of the book) tends to be damaged. A bookbinder of FIGS. 5 to 10 according to a second preferred embodiment of the invention is free from such a defect. As shown, e.g., in FIG. 6, the bookbinder according to the second preferred embodiment of the invention comprises a pair of opposed covers 1 and a spine member 2. The covers 1 each have substantially the same size as sheets of paper to be held together. The spine member 2 is formed with an adhesive face 3 at its inner surface. A release agent is applied to one side portion 5 (indicated by oblique lines) of the outer surface of one of the covers 1. The spine member 2 is attached, at opposed side portions of its adhesive face 3, to part of the portion 5 of the outer surface of one of the covers 5 and the opposite part of the outer surface of the other cover 1. In FIG. 10, the spine member 2 is stripped from the cover 1 having the foregoing side portion 5.

Figure 8:
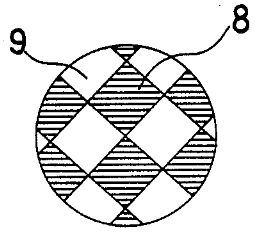
FIG. 8 shows an example of the manner of applying a release agent to one of opposed covers of the bookbinder of FIG. 5.
Figure 9:
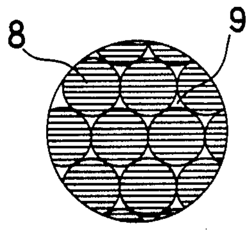
FIG. 9 shows another example of the manner of applying a release agent to one of opposed covers of the bookbinder of FIG. 5.

A conventional fluoric or silicic release agent prepared to provide suitable adhesive and parting properties may be used as the release agent. The "suitable" adhesive and parting properties of the release agent herein mean its adhesive property which does not allow the spine member 2 to separate naturally from the foregoing one side portion 5 of the cover after sheets of paper have been held together and the whole placed on a flat surface at its upright position, as well as its property of allowing the spine member 2 to be manually stripped from the portion 5 of the cover without causing damage to the cover or the member 2. If required to improve such "suitable" properties of the release agent, the agent may be applied to the portion 5 not wholly, but in a selected manner such as that shown in FIGS. 8 or 9. In FIGS. 8 and 9, numeral 8 designates portions to which the agent is applied, and numeral 9 designates portions to which the agent is not applied. Also, if desired, the release agent may be applied not directly to the portion 5, but to a separate material such as a tape or film of desired material, and such a material may be attached to the portion 5 in a permanent manner.

In certain cases, the release agent may be applied not to the portion 5, but to the entire outer surface of the cover or to an area within the portion 5 which is a little smaller than the area of the portion 5. Also, if desired, the release agent may be applied not only to the portion 5, but also to the opposite portion of the other cover.

Figure 5:
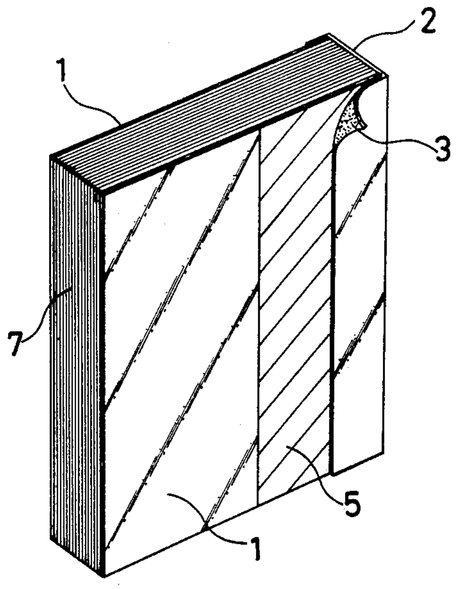
FIG. 5 shows sheets of paper, such as postal cards, held together with a bookbinder according to a second preferred embodiment of the invention.
Figure 6:
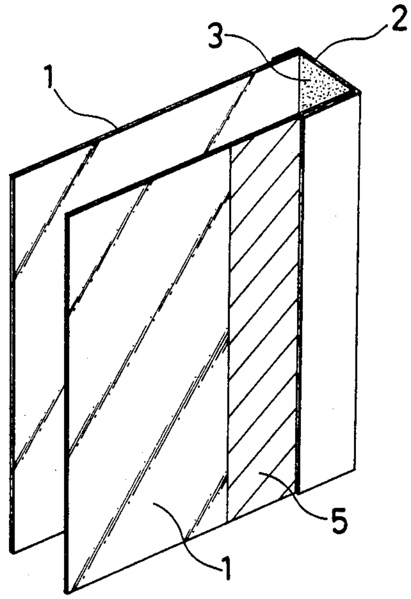
FIGS. 6 and 7 each show the bookbinder used in FIG. 5.
Figure 7:
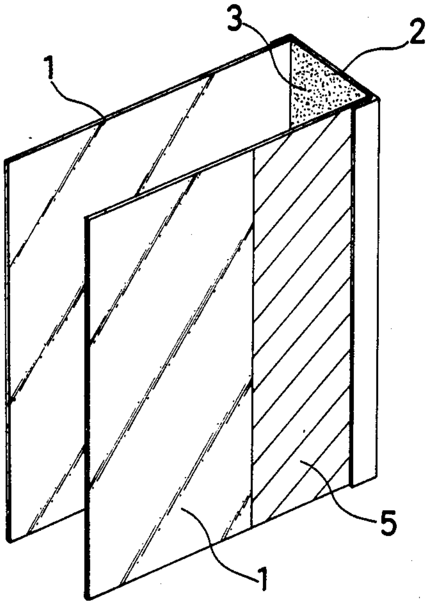

Before the bookbinder of the second embodiment is supplied to a user, a sheet of paper (not shown) is attached to the exposed portion of the adhesive face 3 for protection thereof, as in the case of the first embodiment. For use, first the sheet attached to the exposed portion of the face 3 is peeled, and the spine member 2 is detached from one of the covers 1. Then, as shown in FIG. 3, sheets of paper to be held together, such as postal cards, are placed on the cover to which the spine member 2 is attached, and the other cover is placed on the uppermost sheet. Then as shown in FIG. 3, the spine member 2 is bent in a direction indicated by the arrow and is attached, at its adhesive face 3, to one side of the whole of the sheets. The side portion of the spine member 2 opposite to its side portion attached to the lower cover is attached to the upper cover. Thus the sheets 7 are held together as if a book were bound, as shown in FIG. 5. If, thereafter, it is desired to add a new sheet or sheets to the book or to remove one or more of the existing sheets 7 therefrom, preparations for the desired addition or removal can be made only by stripping the spine member 2 from both the portion 5 and the sheets 7. Since the release agent is applied to the portion 5, the spine member can be readily and smoothly stripped therefrom without causing damage to the spine member or the cover and with no adhesive of the member 2 left on the cover. After the desired addition or removal, the foregoing operation may be repeated to rebind the book. If a certain number of new sheets have been added, the spine proper may have a thickness as shown in FIG. 7.

If desired, the bookbinder of the second embodiment may be supplied to a user in a configuration where the opposed covers are in contact with each other and the greater part of the spine member is attached to the cover having the portion 5 (not shown). Also, if desired, the bookbinder of the second embodiment may be supplied to a user in a configuration where the spine member is detached from the cover having the portion 5 (FIG. 10) or detached from both covers (not shown). In such a case, a sheet of paper is attached to the exposed portion of the adhesive face 3 of the spine member or the entire adhesive face 3 for protection thereof.

Figure 12:
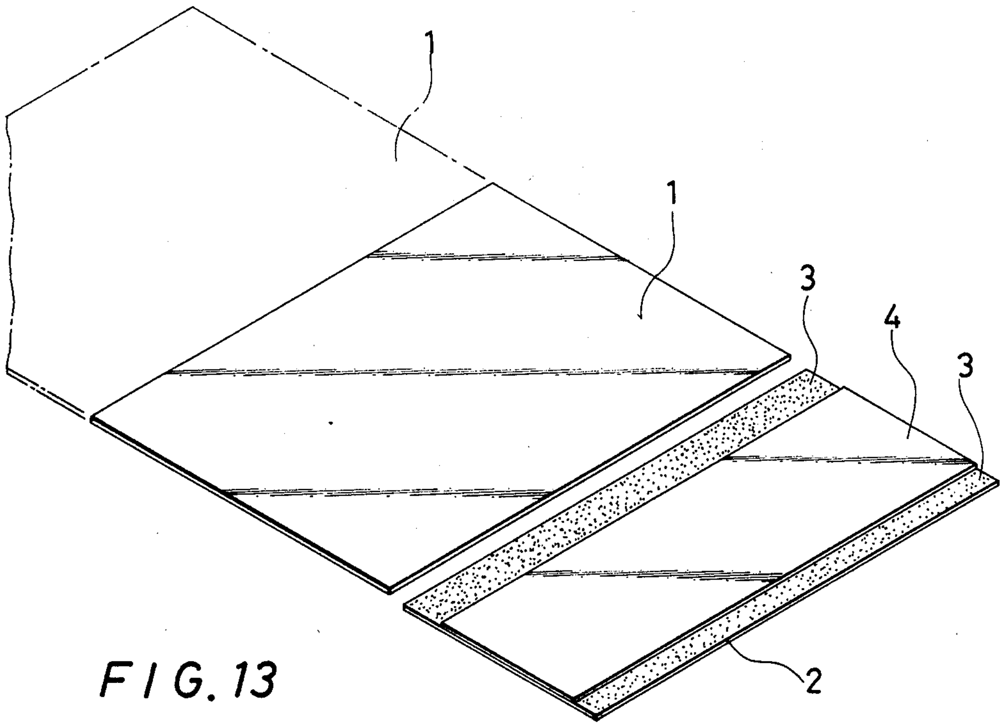
FIG. 12 is an exploded view of the bookbinder of FIG. 11.
Figure 13:
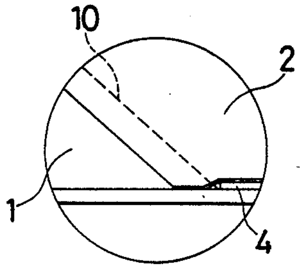
FIG. 13 shows a portion of a row of short cuts made in a spine member of the bookbinder of FIG. 11 to permit the ready separation of the spine member from a cover of the bookbinder.

FIG. 11 shows a bookbinder according to a third preferred embodiment of the invention. The bookbinder of FIG. 11 comprises a cover 1 and a spine member 2. The cover 1 has substantially the same size as sheets of paper to be held together. As shown in FIG. 12 which is an exploded view of the bookbinder of FIG. 11, the spine member 2 is formed with an adhesive face 3 at one of its opposed surfaces. The greater part of the adhesive face 3 is covered with a sheet of paper 4 for protection thereof. Opposed side portions of the adhesive face 3 are exposed to the outside before assembling the bookbinder as shown in FIG. 11. The bookbinder of FIG. 11 is assembled by attaching one of the exposed side portions of the adhesive face 3 to one side portion of one of the opposed surfaces of the cover 1, turning up the rest of the member 2 and attaching the other exposed side portion of the face 3 to the middle of the other surface of the cover 1. As illustrated in FIG. 13, the member 2 is provided with a row of short cuts 10 along the boundary between the side portion of the face 3 attached to the middle of the cover and the adjacent side of the protective sheet 4. FIG. 13 shows a portion of the row of the short cuts 10. The short cuts 10 permit the ready separation of the member 2 into two along the foregoing boundary. If desired, instead of the short cuts 10, any other kind of means to facilitate the foregoing separation may be provided along the foregoing boundary. For use, first the spine member 2 is separated into two along the foregoing boundary, and then the greater part of the member 2 is turned up to the right side in FIG. 11. The smaller part of the member 2 remaining on the cover 1 is stripped from the cover or, if it is not necessary to do so, is left on the cover as it is. Then, sheets of paper to be held together, such as postal cards, are placed on the cover 1 (FIG. 3), and the protective paper 4 is stripped from the spine member 2. All subsequent operations to be made to hold the sheets together, as well as the manner of the addition of a new sheet or sheets or the removal of one or more of the existing sheets after the binding of a book, are the same as in the case of the first embodiment.

Figure 14:
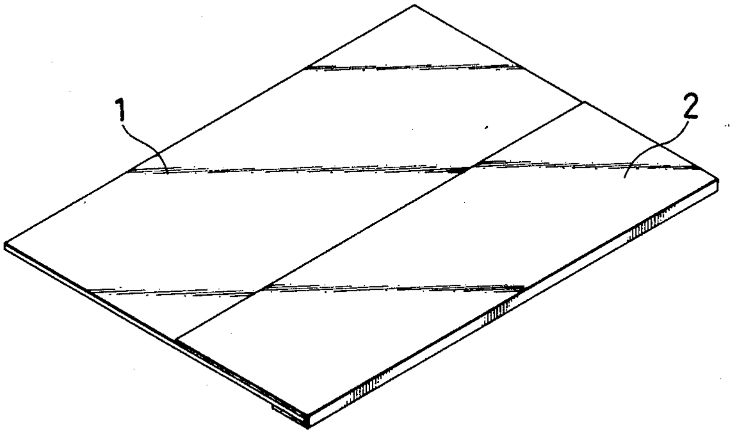
FIG. 14 is a perspective view of a bookbinder according to a fourth preferred embodiment of the invention.
Figure 15:
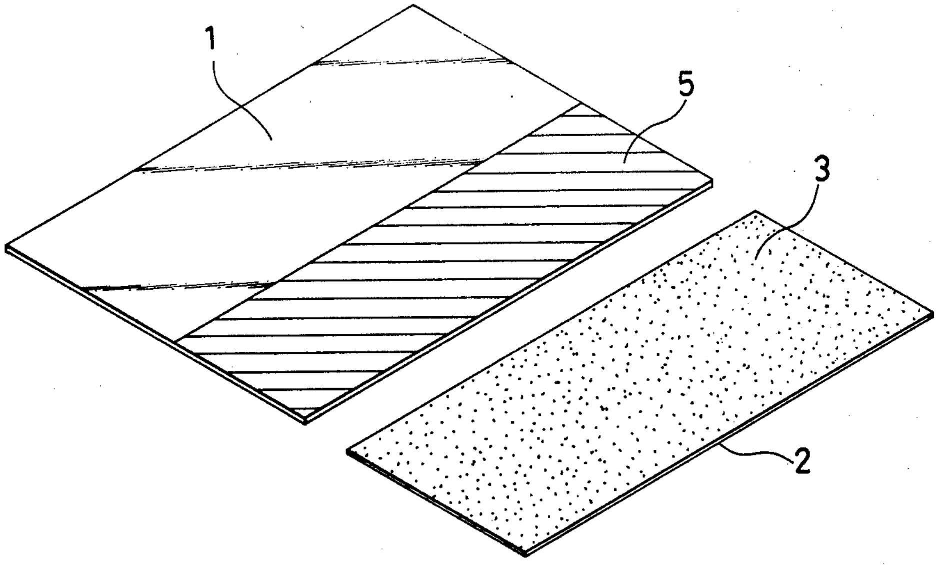
FIG. 15 is an exploded view of the bookbinder of FIG. 14.
Figure 16:
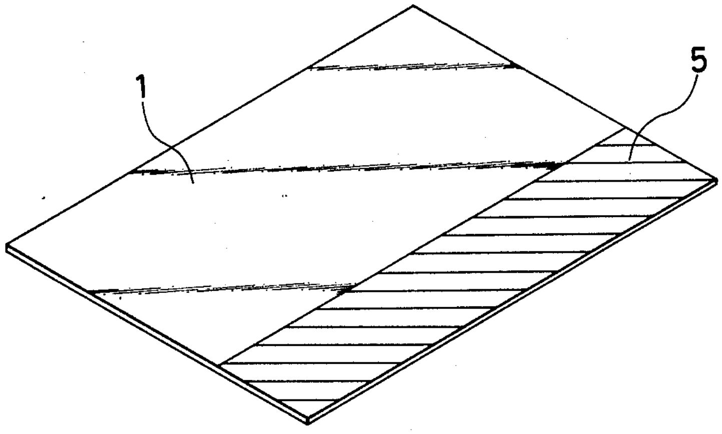
FIG. 16 shows a modification of the bookbinder of FIG. 14.

FIG. 14 shows a bookbinder according to a fourth preferred embodiment of the invention. The bookbinder of FIG. 11 comprises a cover 1 and a spine member 2. The cover 1 has substantially the same size as sheets of paper to be held together. As shown in FIG. 15 which is an exploded view of the bookbinder of FIG. 14, the spine member 2 is formed with an adhesive face 3 at one of its opposed surfaces. The adhesive face 3 is not covered with any protective sheet of paper. The same release agent as used for the bookbinder of the second embodiment is applied to one of the opposed surfaces of the cover 1 at its one side portion 5 indicated by oblique lines. The bookbinder of FIG. 15 is assembled by attaching one side portion of the adhesive face 3 of the member 2 to the surface of the cover 1 to which no release agent is applied, turning up the rest of the member 2 and attaching the rest of the member 2 to the side portion 5 of the opposed surface of the cover. If desired, the release agent may be applied to a smaller portion of the cover than the portion 5 of FIG. 15, as shown in FIG. 16, although in such a case the turned-up portion of the spine member 2 is only partly brought into contact with the release agent. For use, first the spine member 2 is stripped from the side portion 5 of the cover, and is turned up to the right side in FIG. 14. All subsequent operations to be made to hold desired sheets of paper together, as well as the manner of the addition of a new sheet or sheets or the removal of one or more of the existing sheets after the binding of a book, are the same as in the case of the first embodiment.

It will be appreciated that both the bookbinder of FIG. 11 according to the third embodiment of the invention and the bookbinder of FIG. 14 according to the fourth embodiment thereof are more similar, in their entire shapes, to a postcard, a business card or similar cards than the bookbinders of the other embodiments. Therefore, the bookbinders of FIGS. 11 and 14 may be used not only as such, but also as a postcard, a business card or the like. For use as a postcard or a business card, the name, address and other information may be typed, written by hand or printed on either bookbinder. And the person who receives such a card may use the card in its truly intended function, i.e., as a bookbinder.

The adhesive face 3 of the spine member 2 may be formed of any suitable commercially available adhesive agent or pressure sensitive adhesive double coated tape. The amount of the adhesive agent to be used may be determined on the basis of the desired adhesive properties.

The bookbinder according to any of the foregoing embodiments of the invention has a very simple construction, and may be manufactured at a very low cost. Also, the bookbinder enables a non-professional to hold together sheets of paper very easily and instantly. Thus the bookbinder has a great practical value.

What is claimed is:

1. A document binding apparatus for holding together sheets of paper, including postal cards, calling cards, business cards, and photographs, comprising:

(a) first and second covers;

(b) a release agent applied to a portion of one surface of the first cover;

(c) a spine member of a predetermined width having an adhesive face on one surface thereof, wherein a portion of the adhesive surface is attached to one surface of the second cover and another portion of the adhesive surface is removably attached to the release agent of the first cover; and (d) a removable sheet of release paper attached, the protection, to the portion of the adhesive surface of the spine member not attached to the first or second cover, said release paper being removable from the spine member to expose the adhesive surface for binding documents within the apparatus.

2. A document binding apparatus for holding together sheets of paper, including postal cards, calling cards, business cards and photographs, comprising:

(a) a cover; and (b) a spine member of a predetermined width having an adhesive face on one surface thereof, with a removable sheet of release paper protecting a central, greater portion of the adhesive surface of the spine member, while allowing opposed first and second adhesive strips to remain exposed, the first adhesive strip being attached to one surface of the cover;

said release paper being removable from the spine member to expose the adhesive surface to assist the second adhesive strip in binding documents within the apparatus. , 3. The apparatus of claim 2 wherein said cover has substantially the same size and shape as a usual business card.

4. The apparatus of claim 2 wherein said cover has substantially the same size and shape as a usual postcard.

5. A document binding apparatus for holding together sheets of paper, including postal cards, calling cards, business cards and photographs, comprising:

(a) a cover having a release agent applied to a portion of one surface thereof; and (b) a spine member of a predetermined with having an adhesive face on one surface thereof wherein a portion of said adhesive face of the spine member is secured to a surface of the cover opposite the release agent and the remainder of said adhesive face of the spine member is adapted to bind documents within the apparatus.

6. The apparatus of claim 5 wherein said cover has substantially the same size and shape as a usual business card.

7. The apparatus of claim 5 wherein said cover has substantially the same size and shape as usual postcard.

* * * * *